(12) United States Patent
Jutila et al.

(10) Patent No.: US 11,850,182 B2
(45) Date of Patent: *Dec. 26, 2023

(54) INSERTER

(71) Applicant: Bayer Oy, Turku (FI)

(72) Inventors: Ilkka Jutila, Littoinen (FI); Heikki Lyytikäinen, Nanntali (FI); Ulla Calvo Alonso, Piispanristi (FI); Taina Tjäder, Littoinen (FI); Marjo Ali-Äijälä, Preitilä (FI)

(73) Assignee: Bayer Oy, Turku (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,236

(22) Filed: May 12, 2022

(65) Prior Publication Data

US 2022/0265465 A1 Aug. 25, 2022

Related U.S. Application Data

(63) Continuation of application No. 17/239,417, filed on Apr. 23, 2021, which is a continuation of application (Continued)

(30) Foreign Application Priority Data

Sep. 17, 2008 (FI) ...................................... 20080523

(51) Int. Cl.
*A61F 6/18* (2006.01)
*A61F 6/14* (2006.01)
(52) U.S. Cl.
CPC ................ *A61F 6/18* (2013.01); *A61F 6/142* (2013.01); *A61F 6/144* (2013.01)
(58) Field of Classification Search
CPC ...... A61F 6/18; A61F 6/14; A61F 6/06; A61F 6/00; A61F 6/12; A61F 6/142; A61F 6/144
(Continued)

(56) References Cited

U.S. PATENT DOCUMENTS 3,533,406 A 10/1970 Tatum
3,656,483 A 4/1972 Rudel
(Continued)

FOREIGN PATENT DOCUMENTS

CA 1033247 6/1978
CN 1377635 11/2002
(Continued)

OTHER PUBLICATIONS

USPTO, Non-final Office Action for U.S. Appl. No. 17/239,417, dated Dec. 22, 2022, 18 pages.
(Continued)

*Primary Examiner* — Victoria Hicks Fisher
(74) *Attorney, Agent, or Firm* — IP Spring

(57) ABSTRACT

The invention relates to an inserter for an intrauterine system, including a handle (3) having a longitudinal opening (8) at its first end, the opening (8) having a longitudinal axis parallel to the longitudinal axis of the inserter, a first end (8a) and a second end (8b), a moveable slider (5) arranged in the longitudinal opening (8) and having a first end (5a) and a second end (5b), a plunger (2) attached to the handle (3), an insertion tube (6) arranged around the plunger (2) having a first end and a second end, with its second end attached to the slider (5). The inserter further includes a lock that reversibly locks locking the intrauterine system in relation to the plunger (2) via a removal string of the intrauterine system, the lock being controllable by the slider (5) and/or the insertion tube (6).

16 Claims, 9 Drawing Sheets

Related U.S. Application Data

No. 15/589,789, filed on May 8, 2017, now Pat. No. 10,987,244, which is a continuation of application No. 13/119,397, filed as application No. PCT/FI2009/050735 on Sep. 14, 2009, now Pat. No. 9,668,912.

(58) Field of Classification Search
USPC .......................................................... 128/830
See application file for complete search history.

(56) References Cited

U.S. PATENT DOCUMENTS

| | | | |
|---|---|---|---|
| 3,783,861 A | 1/1974 | Abramson | |
| 3,794,025 A | 2/1974 | Lerner | |
| 3,896,819 A | 7/1975 | Zaffaroni et al. | |
| 3,902,483 A | 9/1975 | Place et al. | |
| 3,918,444 A | 11/1975 | Hoff et al. | |
| 4,143,656 A | 3/1979 | Holmes | |
| 4,341,728 A | 7/1982 | Robertson et al. | |
| 4,353,363 A | 10/1982 | Sopena | |
| 4,413,985 A | 11/1983 | Wellner et al. | |
| 4,562,835 A | 1/1986 | Anderson | |
| 4,578,075 A | 3/1986 | Urquhart et al. | |
| 4,578,076 A | 3/1986 | Luukkainen et al. | |
| 4,655,204 A | 4/1987 | Basuyaux | |
| 4,678,463 A | 7/1987 | Millar | |
| 4,721,105 A | 1/1988 | Wildemeersch | |
| 4,724,832 A | 2/1988 | Strubel et al. | |
| 4,805,628 A | 2/1989 | Fry et al. | |
| 4,949,732 A | 8/1990 | Spoon et al. | |
| 5,146,931 A | 9/1992 | Kurz | |
| 5,217,450 A | 6/1993 | Pryor et al. | |
| 5,224,493 A | 7/1993 | Sawan et al. | |
| 5,370,129 A | 12/1994 | Diaz et al. | |
| 5,494,047 A | 2/1996 | Van Os | |
| 5,785,053 A * | 7/1998 | Macandrew | A61F 6/18 606/119 |
| 6,056,976 A | 5/2000 | Markkula et al. | |
| 6,103,256 A | 8/2000 | Nabahi | |
| 6,119,696 A | 9/2000 | Turin | |
| 6,278,057 B1 | 8/2001 | Avellanet | |
| 6,299,027 B1 | 10/2001 | Berge et al. | |
| 6,476,079 B1 | 11/2002 | Jukarainen et al. | |
| 6,588,429 B1 | 7/2003 | Wildemeersch | |
| 6,652,548 B2 | 11/2003 | Evans et al. | |
| D525,705 S | 7/2006 | Luukkainen | |
| 7,252,839 B2 | 8/2007 | Hallinen et al. | |
| 7,294,135 B2 | 11/2007 | Stephens et al. | |
| 7,926,488 B2 | 4/2011 | Luukkainen | |
| 8,573,222 B2 | 11/2013 | Weintraub | |
| D718,435 S | 11/2014 | Deckman et al. | |
| 9,452,082 B2 | 9/2016 | Lyytikainen et al. | |
| 9,615,965 B2 * | 4/2017 | Lyytikäinen | A61F 6/142 |
| 9,668,912 B2 | 6/2017 | Jutila et al. | |
| D791,318 S | 7/2017 | Jutila et al. | |
| 9,707,123 B2 | 7/2017 | Lyytikainen et al. | |
| D810,289 S | 2/2018 | Jutila et al. | |
| 10,149,784 B2 | 12/2018 | Jutila et al. | |
| 10,561,524 B2 | 2/2020 | Lyytikainen et al. | |
| 10,583,035 B2 | 3/2020 | Lyytikainen et al. | |
| 10,987,244 B2 | 4/2021 | Jutila et al. | |
| 11,432,958 B2 | 9/2022 | Lyytikäinen et al. | |
| 2004/0261799 A1 | 12/2004 | Mock | |
| 2005/0178391 A1 | 8/2005 | Wildemeersch | |
| 2007/0056591 A1 | 3/2007 | McSwain | |
| 2007/0129734 A1 | 6/2007 | Jutila | |
| 2008/0095825 A1 | 4/2008 | Lafont | |
| 2009/0123522 A1 | 5/2009 | Browning | |
| 2010/0168563 A1 | 7/2010 | Braver | |
| 2010/0186750 A1 | 7/2010 | Tran et al. | |
| 2010/0280464 A1 | 11/2010 | De Graaff et al. | |
| 2011/0017219 A1 | 1/2011 | De Graaff et al. | |
| 2011/0056501 A1 | 3/2011 | Kortesuo et al. | |
| 2011/0061659 A1 | 3/2011 | Cruzada et al. | |
| 2011/0146693 A1 | 6/2011 | Duesterberg et al. | |
| 2011/0162656 A1 | 7/2011 | Jutila et al. | |
| 2011/0166508 A1 | 7/2011 | Lyytikainen et al. | |
| 2011/0172593 A1 | 7/2011 | Lyyikäinen et al. | |
| 2011/0226257 A1 | 9/2011 | Lowe et al. | |
| 2013/0255695 A1 | 10/2013 | Jutila et al. | |
| 2015/0107598 A1 | 4/2015 | Tal et al. | |
| 2016/0217707 A1 | 7/2016 | Jutila | |
| 2017/0027739 A1 | 2/2017 | Deckman et al. | |
| 2017/0196728 A1 | 7/2017 | Lyytikainen et al. | |
| 2017/0202701 A1 | 7/2017 | Tal et al. | |
| 2020/0179159 A1 | 6/2020 | Lyytikainen et al. | |
| 2021/0298942 A1 | 9/2021 | Jutila et al. | |
| 2022/0265466 A1 | 8/2022 | Jutila et al. | |
| 2022/0273487 A1 | 9/2022 | Jutila et al. | |

FOREIGN PATENT DOCUMENTS

| | | |
|---|---|---|
| CN | 201042478 | 4/2008 |
| DE | 8712168 | 10/1987 |
| DE | 29819558 | 2/1999 |
| DE | 19815552 | 9/1999 |
| DE | 29919662 | 3/2000 |
| EP | 0191957 | 8/1986 |
| EP | 0798999 | 10/1997 |
| EP | 0948948 | 10/1999 |
| EP | 1691740 | 8/2006 |
| FI | 882466 | 11/1999 |
| FI | 0080523 | 9/2008 |
| GB | 1039011 | 8/1966 |
| GB | 1403393 | 8/1975 |
| GB | 1486994 | 9/1977 |
| GB | 1543841 | 4/1979 |
| JP | 2010-510444 | 4/2010 |
| NL | 8601570 | 1/1988 |
| RU | 1377063 | 2/1988 |
| WO | 95/28901 | 11/1995 |
| WO | 1995028901 A1 | 11/1995 |
| WO | 96/18365 | 6/1996 |
| WO | 1996/18365 | 6/1996 |
| WO | 1996/029026 | 9/1996 |
| WO | 1999/005958 | 2/1999 |
| WO | 00/00550 | 1/2000 |
| WO | 2001/013832 | 3/2001 |
| WO | 03/017971 | 3/2003 |
| WO | 2005/048893 | 6/2006 |
| WO | 2007/075086 | 7/2007 |
| WO | 2010/031900 A1 | 3/2010 |
| WO | 2010/031902 | 3/2010 |
| WO | 2010/082197 | 7/2010 |
| WO | 2010/112095 | 10/2010 |
| WO | 2011/080164 | 7/2011 |

OTHER PUBLICATIONS

USPTO, Final Office Action for U.S. Appl. No. 16/792,748, dated Nov. 29, 2022, 7 pages.

merriam-webster.com, "adhesion", Retrieved from Internet: https://www.merriam-webster.com/dictionary/adhesion, 2023, 1 page.

USPTO, Non-final Office Action for U.S. Appl. No. 17/743,249, dated Feb. 8, 2023, 30 pages.

USPTO, Non-final Office Action for U.S. Appl. No. 17/743,213, dated Jan. 26, 2023, 30 pages.

USPTO, Non-final Office Action for U.S. Appl. No. 17/239,428, dated Jun. 21, 2023, 11 pages.

USPTO, Final Office Action for U.S. Appl. No. 17/239,417, dated May 31, 2023, 21 pages.

USPTO, Final Office Action for U.S. Appl. No. 17/743,213, dated Jun. 14, 2023, 29 pages.

USPTO, Non-final Office Action for U.S. Appl. No. 16/792,748, dated May 10, 2023, 7 pages.

USPTO, Ex Parte Quayle Action for U.S. Appl. No. 17/743,249, Jun. 27, 2023, 7 pages.

USPTO Non-Final Office Action mailed in U.S. Appl. No. 13/119,401, dated Aug. 17, 2012.

USPTO Non-Final Office Action mailed in U.S. Appl. No. 13/771,066, dated May 22, 2013, 10 pages.

USPTO Final Office Action received for U.S. Appl. No. 14/088,329, dated Jan. 30, 2015, 18 pages.

(56) References Cited

OTHER PUBLICATIONS

USPTO Non-Final Office Action received for U.S. Appl. No. 14/088,329, dated Apr. 9, 2014, 19 pages.
USPTO Non-Final Office Action received for U.S. Appl. No. 14/088,329, dated Dec. 3, 2015, 19 pages.
USPTO Non-Final Office Action received in U.S. Appl. No. 13/857,134, dated Jul. 7, 2014, 19 pages.
USPTO Non-Final Office Action received for U.S. Appl. No. 13/119,397, dated Nov. 19, 2013, 19 pages.
EPO Notice of Opposition to European Patent No. EP2352470, dated Sep. 26, 2013, 19 pages.
USPTO Non-Final Office Action received in U.S. Appl. No. 14/590,969, dated Jan. 29, 2016, 20 pages.
USPTO Final Office Action received for U.S. Appl. No. 13/119,397, dated Jan. 12, 2016, 21 pages.
USPTO Non-Final Office Action received in U.S. Appl. No. 13/119,399, dated Oct. 4, 2012, 22 pages.
USPTO Non-Final Office Action received for U.S. Appl. No. 13/119,397, dated May 5, 2015, 23 pages.
EPO Reply to the Notice of Opposition to European Patent No. EP2352470, dated Apr. 25, 2014, 28 pages.
USPTO Final Office Action received for U.S. Appl. No. 13/119,397, dated Sep. 5, 2014, 28 pages.
WIPO, International Preliminary Report on Patentability mailed in PCT Application No. PCT/FI2009/050733, dated Mar. 22, 2011, 6 pages.
WIPO, International Preliminary Report on Patentability mailed in PCT Application No. PCT/FI2009/050735, dated Mar. 22, 2011, 6 pages.
WIPO, International Search Report and Written Opinion mailed in PCT Application No. PCT/FI2009/050735, dated Dec. 10, 2009, 8 pages.
WIPO, International Search Report and Written Opinion mailed in PCT Application No. PCT/FI2009/050733, dated Dec. 23, 2009, 8 pages.
Johnson, et al., "Insertion and Removal of Intrauterine Devices", American Family Physician, vol. 71, No. 1, Jan. 1, 2005, pp. 95-102.
USPTO, Notice of Allowance for U.S. Appl. No. 16/813,340, dated Apr. 22, 2022, 10 pages.
USPTO, Notice of Allowance for U.S. Appl. No. 14/590,969, dated Mar. 8, 2017, 10 pages.
USPTO, Non-final Office Action for U.S. Appl. No. 13/771,066, dated May 22, 2013, 10 pages.
USPTO, Notice of Allowance for U.S. Appl. No. 15/647,104, dated Oct. 18, 2019, 10 pages.
USPTO, Non-final Office Action for U.S. Appl. No. 13/119,401, dated Aug. 17, 2012, 11 pages.
USPTO, Notice of Allowance for U.S. Appl. No. 13/119,397, dated Apr. 5, 2017, 12 pages.
USPTO, Final Office Action for U.S. Appl. No. 14/590,969, dated Jul. 20, 2016, 14 pages.
USPTO, Ex Parte Quayle Action for Design U.S. Appl. No. 29/558,312, Feb. 6, 2017, 16 pages.
USPTO, Non-final Office Action for U.S. Appl. No. 15/589,789, dated Dec. 30, 2019, 17 pages.
USPTO, Non-final Office Action for U.S. Appl. No. 15/589,789, dated May 29, 2019, 17 pages.
USPTO, Notice of Allowance for Design U.S. Appl. No. 29/605,236, dated Oct. 3, 2017, 19 pages.
USPTO, Notice of Allowance for U.S. Appl. No. 15/470,870, dated Nov. 8, 2017, 25 pages.
USPTO, Notice of Allowance for Design U.S. Appl. No. 29/558,312, dated Mar. 8, 2017, 5 pages.
USPTO, Non-final Office Action for U.S. Appl. No. 15/245,042, dated Oct. 11, 2016, 6 pages.
USPTO, Non-final Office Action for U.S. Appl. No. 16/792,748, dated May 20, 2022, 7 pages.
USPTO, Non-final Office Action for U.S. Appl. No. 15/470,870, dated May 23, 2017, 7 pages.
USPTO, Notice of Allowance for U.S. Appl. No. 15/245,042, dated Feb. 10, 2017, 8 pages.
USPTO, Notice of Allowance for U.S. Appl. No. 15/891,187, dated Jun. 21, 2019, 8 pages.
USPTO, Notice of Allowance for U.S. Appl. No. 14/088,329, dated May 18, 2016, 8 pages.
USPTO, Final Office Action for U.S. Appl. No. 15/589,789, dated May 26, 2020, 8 pages.
USPTO, Non-final Office Action for Design U.S. Appl. No. 29/558,311, dated Oct. 24, 2017, 8 pages.
USPTO, Notice of Allowance for U.S. Appl. No. 15/891,187, dated Oct. 9, 2019, 8 pages.
USPTO, Notice of Allowance for U.S. Appl. No. 15/589,789, dated Dec. 31, 2020, 9 pages.
USPTO, Non-final Office Action for U.S. Appl. No. 15/891,187, dated Nov. 2, 2018, 9 pages.
USPTO, Non-final Office Action for U.S. Appl. No. 15/470,870, Examiner to re-issue NFOA: examined cancelled claim set, dated Apr. 17, 2017, 12 pages.
USPTO, Restriction Requirement for U.S. Appl. No. 17/239,417, dated Sep. 19, 2022, 7 pages.
USPTO, Notice of Allowance for U.S. Appl. No. 16/792,748, dated Aug. 30, 2023, 7 pages.
USPTO, Non-final Office Action for U.S. Appl. No. 17/239,417, dated Oct. 3, 2023, 19 pages.
USPTO, Non-final Office Action for U.S. Appl. No. 17/743,213, dated Sep. 26, 2023, 26 pages.
USPTO, Notice of Allowance for U.S. Appl. No. 17/743,249, dated Sep. 8, 2023, 11 pages.

\* cited by examiner

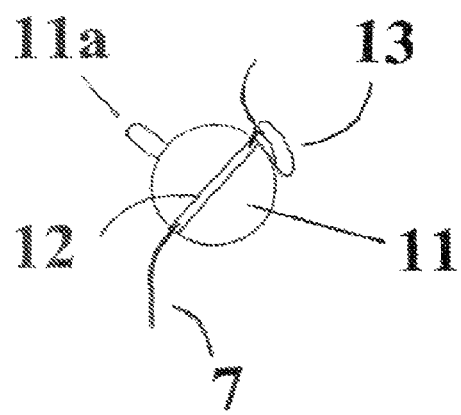 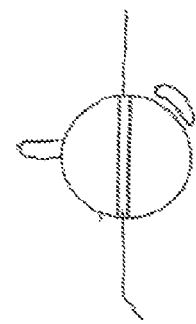
Fig. 5A    Fig. 5B
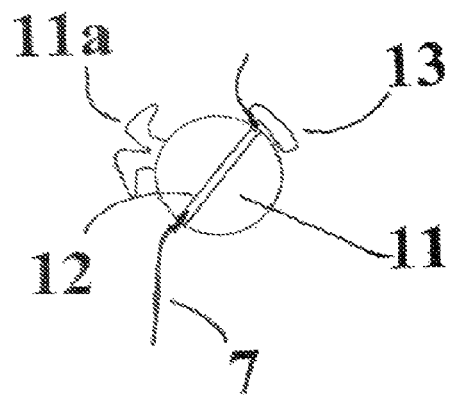 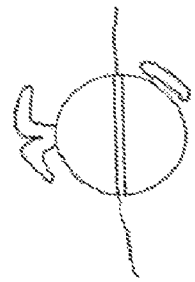
Fig. 6A    Fig. 6B

INSERTER

CROSS REFERENCE TO RELATED APPLICATIONS

This application is a continuation of U.S. patent application Ser. No. 17/239,417, filed Apr. 23, 2021, which is a continuation of U.S. patent application Ser. No. 15/589,789, filed May 8, 2017 (now U.S. Pat. No. 10,987,244), which is a continuation of U.S. patent application Ser. No. 13/119,397, filed Mar. 16, 2011 (now U.S. Pat. No. 9,668,912), which claims priority to International Patent Application No. PCT/FI2009/050735, filed Sep. 14, 2009, which claims priority to Finnish Patent Application No. 20080523, filed Sep. 17, 2008, the contents of all of which are incorporated by reference herein.

SUMMARY

The present invention is related to an inserter for positioning an intrauterine device or an intrauterine system in the uterus.

BACKGROUND OF THE INVENTION

Various types of inserters have been developed for the positioning of mechanical and copper wire-containing intrauterine devices (IUDs) as well as of intrauterine systems having a drug containing cylinder (IUSs). In the following, IUD and IUS can be used interchangeably and when one is mentioned, it is to be understood that either of them can be used. Simple rod-shaped inserters have been suggested for inserting relatively small or sufficiently flexible intrauterine devices in their original, expanded shape by using simple push-in technique. However, most common inserters are constructed for introducing the device into the uterus in a contracted state. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion the device, whether an IUD or an IUS, is usually retracted into the insertion tube either by means of string(s) attached to the device and intended for the removal of the device from the uterus, or by pushing the device into the insertion tube by a plunger with inserters having a special window to adapt the device in the expanded shape (see for example GB 1 403 393). Then the insertion tube with the device therein is introduced through the cervical canal into the uterus. When the device is correctly positioned, it is released either by pushing the plunger towards the uterus or by holding the plunger steady and by retracting the insertion tube outwards. Once expulsed from the insertion tube within the uterine cavity, the device is supposed to resume its original expanded shape.

A typical example of an intrauterine device has a T-shaped body fabricated of plastic material and consisting of an elongated body part having at one end a transverse member comprising two wings, the elongate member and the transverse member forming a substantially T-shaped piece when the device is in the expanded configuration, for example positioned in the uterus. The tips of these wings are preferably hemispherical in order to facilitate the introduction of the device through the cervical canal. The elongate member has a copper spiral or wire or a hormone capsule arranged around the body. The end of the vertical body part has a loop with a string or strings attached to it, with which the device can be removed from the uterus after use or whenever needed.

The diameter of the elongate member in intrauterine systems having a drug containing cylinder is greater than in copper wire-containing IUDs or mechanical devices, and thus the diameter of the insertion tube also has to be larger. However, the frames of these intrauterine systems, or in the commonly used T-shaped systems the hemispherical ends of the transverse member, are small in relation to the diameter of the insertion tube. Therefore the correct positioning of the IUS within the insertion tube is extremely important, and this will only be attained by properly handling the removal string(s) during the preparatory steps and insertion as well as when finally releasing the IUS after insertion. Challenging steps, which will be exemplified with a common T-shaped device, apply as well to intrauterine systems having another type of frame, for example 7-shaped or closed, continuous frames.

For the insertion of a T-shaped intrauterine system it is extremely important that the hemispherical ends of the transverse member are in the exactly correct position in relation to the edge of the insertion tube at the moment of introducing the device in the uterus. If the IUS is pulled into the insertion tube by means of the removal string, which is usually the case with the existing devices, it is understandable that it is difficult to make the IUS stop in the correct position, especially if the relative movement of the insertion tube and the plunger is not restricted by any stop member. Pulling with too much force easily makes these ends enter almost completely into the insertion tube. During the insertion of the device, the sharp edges of the insertion tube may interfere with the introduction of the device through the cervical canal. On the other hand, if the device is not drawn deep enough into the insertion tube, the frame ends project outwardly because of a relatively wide insertion tube. The diameter at the level of the wings remains too wide, which makes the introduction of the device more difficult. It is easier to make the wings stop in the correct position in the case of copper-wire devices, because then the insertion tube is narrow in relation to the wings and therefore there is no risk of the wings being drawn too deep into the tube even by forceful pulling.

When the device is pulled into the insertion tube, it is important that the device is directed onto the plunger in the correct position, i.e. without damaging the loop, the rest of the body or the string(s). If the device is pulled onto the plunger in a wrong position, the edges of the insertion tube or the plunger can damage the loop or the body. If pulling is continued and the device does not turn into the correct position, the string(s) will finally cut through the loop or the body, which can also cause the device to get jammed within the insertion tube or plunger.

The European patent application EP 1 691 740 relates to an inserter, with which the correct positioning and directional stiffness of the device in the inserter prior to and during insertion can be ensured, for instance, by shaping the forward end of the plunger such that the IUS assumes a specified constant configuration when drawn into the insertion tube. The IUS will thus not be twisted during insertion.

European patent EP 798 999 relates to an inserter, which allows the correct positioning of an IUS also in those cases in which the elongate member of a T-shaped device contains active material, which involves a diameter larger than that of an elongate member of a copper-wire IUD. The inserter comprises a plunger, a handle attached to the plunger, a string for the removal of the IUS, a cleft on the end of the handle to lock the string(s) in such a way that the IUS remains immobile in relation to the plunger, and an insertion tube around the plunger. The IUS is drawn into the insertion tube by pushing the tube over the device or by pulling on the removal threads whereafter the threads are manually locked in the cleft. The relative movement of the plunger and the protective tube is restricted by a stop member or stop members to ascertain that the correct configuration of the IUS is achieved. The stop members ensure that the front edge of the insertion tube is stopped in a configuration in which the hemispherical tips of the T-wings remain partly uncovered by the insertion tube but the wings nevertheless remain pressed against each other. This inserter overcomes many of the problems encountered with the conventional inserters, but the string(s) still need to be manually handled and locked.

OBJECT AND SUMMARY OF THE INVENTION

An object of the invention is to provide a simple, easy to use inserter for the positioning of an intrauterine system in the uterus by solving at least partially at least some of the problems mentioned above. An object of the invention is particularly to provide an inserter having an improved system for locking and releasing the removal strings of an IUS in the necessary steps during the insertion process so that no manual handling of the strings as such is needed.

A typical inserter for an intrauterine system according to the present invention, comprises
- a handle having a longitudinal opening at its first end, said opening having a longitudinal axis parallel to the longitudinal axis of the inserter, a first end and a second end,
- a movable slider arranged in said longitudinal opening and having a first end and a second end,
- a plunger attached to the handle,
- an insertion tube arranged around the plunger having a first end and a second end, with its second end attached to the slider.

The inserter is characterized in that it further comprises locking means for reversibly locking the intrauterine system in relation to the plunger via a removal string of the intrauterine system, said locking means being controllable by the slider and/or the insertion tube.

BRIEF DESCRIPTION OF THE DRAWING

FIGS. 5A and 5B illustrate a locking means according to an embodiment of the invention.

FIGS. 6A and 6B illustrate a locking means according to another embodiment of the invention.

DETAILED DESCRIPTION OF THE INVENTION

Figure 1:
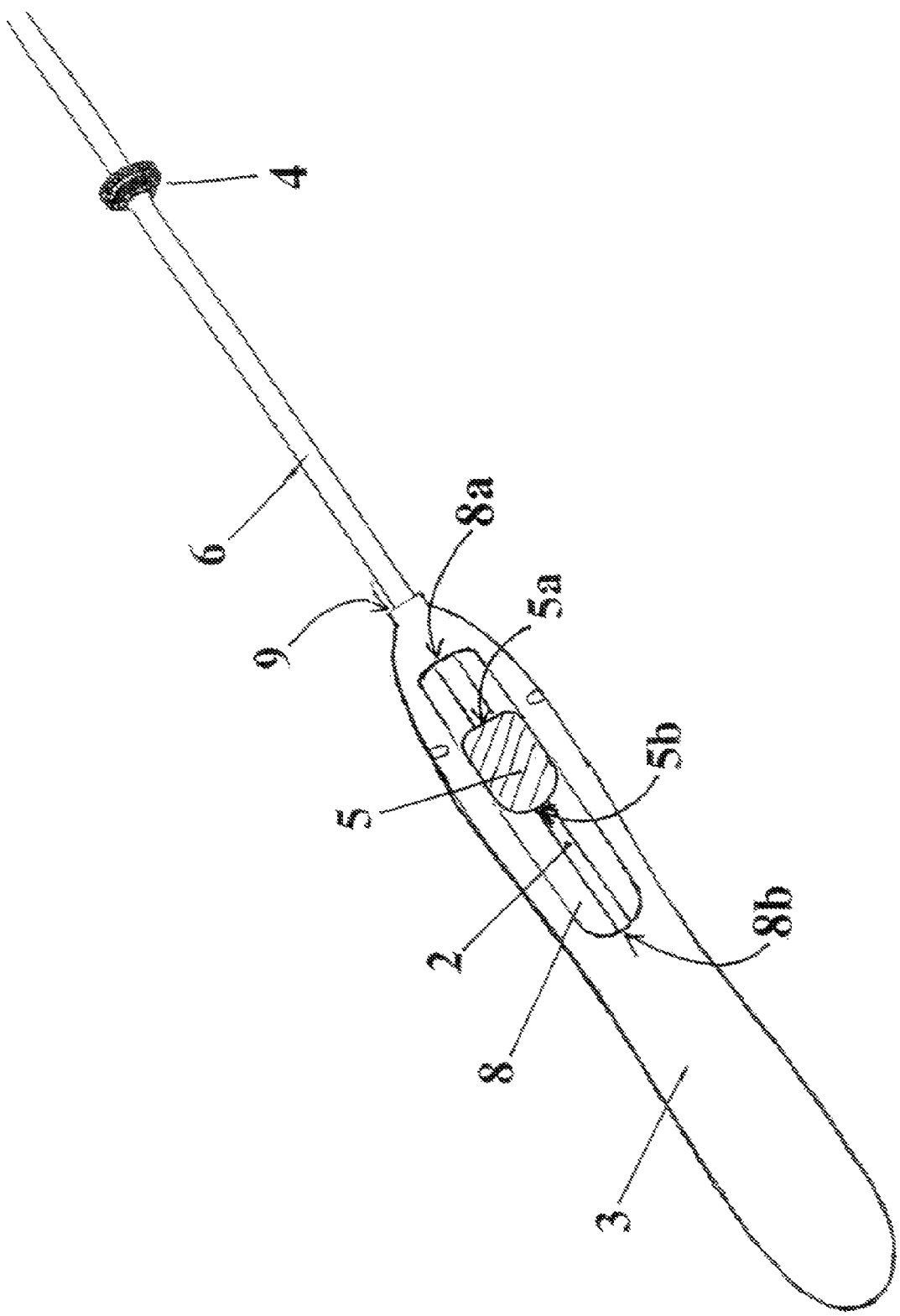
FIG. 1 illustrates a general overview of an inserter according to an embodiment of the invention.

A typical inserter for an intrauterine system according to the present invention, comprises
- a handle having a longitudinal opening at its first end, said opening having a longitudinal axis parallel to the longitudinal axis of the inserter, a first end and a second end,
- a movable slider arranged in said longitudinal opening and having a first end and a second end,
- a plunger attached to the handle,
- an insertion tube arranged around the plunger having a first end and a second end, with its second end attached to the slider and/or the insertion tube.

The inserter is characterized in that it further comprises locking means for reversibly locking the intrauterine system in relation to the plunger via a removal string of the intrauterine system, said locking means being controllable by the slider and/or the insertion tube. This means that the locking means can also be controlled by a part of the slider and/or of the insertion tube, such as an extension of either or both of them.

The inserter according to the present invention thus comprises means for reversibly locking the intrauterine system, for example by locking the removal string or strings of the intrauterine system, in such a way that the device remains immobile in relation to the plunger during the necessary steps prior to insertion and during insertion but can be released after the IUS has correctly been positioned in the uterus. Moreover, with the present invention, no manual handling of the strings as such is needed, which increases security and hygiene.

The longitudinal opening on the handle can have be also quite narrow and does not need to be symmetrically positioned on the handle and with respect to the longitudinal axis.

The invention therefore provides an easy to use inserter, by which only few simple steps are needed to prepare for the insertion and to securely install and position an intrauterine system into the uterus.

In the present description and claims, by first ends are typically meant the ends that are closer to the uterus during the insertion of the intrauterine system. Second ends are the ends opposite to the first ends. Moreover, the terms IUS or IUD are used when describing the preferred embodiment of the present invention, but these are not to be construed as limiting the claims. The term removal string means one or more strings used for removing the system once it reaches the end of its use time. There may thus be one or more such strings, and this term encompasses also strings that are not used for removal but only for locking the device during insertion.

According to one embodiment of the invention, the inserter comprises stop members to control the movement of the slider.

According to a preferable embodiment of the invention, the first end of the opening and the first end of the slider form a first pair of stop members, and the second end of the opening and the second end of the slider form a second pair of stop members.

A part of the handle thus comprises an opening having a first end and a second end and running in the longitudinal direction of the plunger. The handle also has at its first end a channel in which the insertion tube can slide in the longitudinal direction. At the second end, i.e. distal end (away from the uterus) the insertion tube is attached to the slider or to a means which can be used to move the slider and preferably forms at least a part of the slider. With respect to the starting configuration, the front surface of said means and the surface at the first end of the opening (the end directed towards the IUS) together form the first pair of stop members. By simply pushing the slider or the means for moving the slider forwards in the opening the slider arrangement and the insertion tube attached to it can be moved in relation to the plunger to push the insertion tube past the plunger at distance, which corresponds substantially to the length of the IUS assembled for insertion. Because the string(s) and the IUS remain immobile all the time, the IUS is retracted in the insertion tube. To release the IUS after it has been positioned in the uterus the slider and the insertion tube will be pulled backwards past the plunger the distance determined by the second pair of stop members, formed by the rear surface of the means to move the slider and the surface at the second end of the opening.

The handle can have many shapes and is preferably designed for easy handling of the inserter even by using only one hand. The plunger attached to the handle is advantageously hollow or has a groove or bore running in the axial direction thus allowing the string(s) to slide freely in it, without any risk of them getting jammed between the plunger and the insertion tube. The first end, i.e. the forward end of the plunger is preferably suitably shaped to have for example a notch, an indentation, an eyelet, a funnel or a groove to adapt to the lower end of the intrauterine system and to enable the optimal and secure positioning of the intrauterine system on the plunger so that the probability of damage to the intrauterine system is minimal. Thus the IUS will not be twisted when it is drawn in the insertion tube or during insertion and assumes a specified constant configuration when released.

The forward parts (parts directed towards the uterus) of the plunger and the insertion tube can be straight or curved so as to conform to the anatomy of the uterus. Preferably these parts are made from a flexible material in order to avoid perforation of the uterus.

The slider mechanism is preferably inside the handle and comprises at least one elongated element, which can be moved in the longitudinal direction of the plunger. According to an embodiment of the invention the slider comprises means to move the slider, which preferably is a part of the slider, and the insertion tube attached to said means. According to another embodiment of the invention the slider comprises at least two elements, preferably parallel, which are combined on at least one point by a transversal member. The transversal member may form means, for example a knob or switch, by which the slider can be moved. The handle can comprise one or more means to connect the slider elements and to facilitate the movement of the slider, for example a support, a shoulder, a holder, a saddle, a groove or a slot. The slider preferably comprises at least one structural element, for example an extension, which is capable to generate the necessary operation of the locking means to keep the strings immobilized during storage or during preparatory steps before insertion or during insertion and/or to release the string(s) when the slider is moved to the backward position.

The locking means is a lock which, induced by the movement of the slider or of the means to move the slider and the insertion tube, can immobilise the removal string(s) to hold the IUS in a stable position and/or to release the string(s) after insertion to release the IUS. Particularly, the invention relates to a locking means which comprises an object capable of reversibly preventing and/or allowing the movement of the string(s) by at least partly moving or pivoting from the original position, for example rotating around a shaft or an axle, and vertically or horizontally attached to the handle. The object may have several shapes and may be for example round or rod-shaped, wedge, polygonal or rectangular with rounded or sharp corners. The surface of the object preferably comprises one or more extensions having variable size and shape, for example a knob, a rib or a switch. When the slider mechanism is moving backwards, at a suitable point a part or an extension of the slider or of the insertion tube is pressed against at least one extension of the object thus changing its orientation enough relative to the original position to cause release of the string(s). Preferably the object has a slot or pinhole through which the string(s) run. The locking means may also comprise at least one counterpart against which the string(s) are pressed by the object and thus reversibly immobilized in the locking position. The counterpart has a suitable shape adapted to fit at least some part of the surface of the object. An extension, or extensions of the object can be used to keep the object and the counterpart in a fixed configuration until the slider is moved backwards to release the IUS. The counterpart preferably has a suitable design to keep the string(s) in proper direction, for example a slot or pinhole through which the string(s) run. Further, the object and said at least one counterpart have preferably a suitable length and diameter to fit inside the handle.

According to one embodiment of the invention, the locking means thus comprises
  a main part,
  a first extension of the main part having an abutment surface,
  a counterpart adapted to form a blocking together with the main part,
wherein the locking means is rotatably mounted on the inserter.

According to another embodiment of the invention the main part comprises an opening or a slot in a diagonal direction through essentially the whole diameter of the main part, adapted to receive at least one removal string of the intrauterine system.

According to yet another embodiment of the invention, the locking means comprises
  a main part,
  a first extension of the main part having an abutment surface,
  a second extension of the main part having a wedge-like shape,
  a counterpart,
wherein the second extension is adapted to form a blocking together with the counterpart and the locking means is rotatably mounted on the inserter.

The locking means can be for example mounted on the handle of the inserter. According to one embodiment of the invention, the main part has essentially the shape of a cylinder, or it is of triangular shape, or of any other suitable shape.

According to one embodiment of the invention the slider comprises an extension adapted to abut on the abutment surface of the first extension of the main part of the locking means.

According to one other embodiment of the invention the locking means comprises a main part comprising a first extension and a second extension arranged, in their initial position, to be essentially in contact with each other to from a blocking, and wherein the slider, a part of the slider, the insertion tube or a part of the insertion tube is arranged to protrude into the main part of the locking means so as to separate the first and second extensions from each other.

According to yet one other embodiment of the invention the locking means comprises
- a first locking part and a second locking part movably mounted on the inserter and arranged, in their initial position, to be essentially in contact with each other to form a blocking, and
- a first protrusion and a second protrusion arranged on a location selected from the group consisting of the inner surface of the insertion tube, the outer surface of the insertion tube, the inner surface of the slider and the outer surface of the slider, wherein the first and second protrusions are arranged so as to move the first and second locking parts to a second position when moving the insertion tube.

The locking means could also be welding, gluing, cutting, knot or adhesion. The strings could thus be for example attached to the body of the inserter by welding (for example by heating), gluing with glue or attaching with an adhesive agent (such as sticker). The slider would then release the attachment when moving to release the device. Other options could be a knot or other mechanical hindrance, when the slot provided for the strings is larger in the releasing position. The slider could also comprise a blade that cuts the strings loose from the inserter.

It is obvious to a person skilled in the art that, in accordance with the above description, the locking means can be of any other kind than those specifically listed above as well as a combination of any of the embodiments and features described above.

According to another embodiment of the invention, the inserter further comprises a flange arranged on the insertion tube. This flange can be adjusted to correspond to the depth of the uterus in order to correctly position the device during its insertion.

The inserter according to the invention is suitable for the positioning of intrauterine devices and intrauterine systems having different sizes and shapes as long as these can be managed to enter the insertion tube by appropriate arrangements.

During the preparatory steps the string(s) are locked but they are released automatically by the slider, when it is drawn backwards in order to release the IUS. Compared to previous inserters, there is no need to manually handle the removal strings during the preparatory steps and during insertion, which eliminates the possibility of user-made mistakes.

The invention further relates to a kit comprising an intrauterine system and an inserter according to the present invention. The intrauterine system can be any device known in the art. Any details and embodiments listed above naturally apply mutatis mutandis to the kit according to the invention.

The present invention also relates to a method for positioning a intrauterine system in a uterus of a patient, wherein the method uses an inserter according to the present invention. The method comprises the steps of
- moving the slider towards the first end of the opening until the first end of the opening is in contact with the first end of the slider, and the intrauterine system is substantially inside the insertion tube,
- introducing the inserter into the uterus of the patient until the intrauterine system is in its correct location,
- moving the slider towards the second end of the opening until the second end of the opening is in contact with the second end of the slider, thus releasing the intrauterine system from the inserter,
- removing the inserter from the uterus of the patient.

The method advantageously contains, at its beginning, the further steps of sounding the uterus using a probe, and setting the flange accordingly to show the correct insertion depth.

An example of the method for positioning the intrauterine system is given hereafter. To insert the IUS only few steps are needed. To prepare for the insertion the sterile package is carefully opened. The IUS is in a correct configuration relative to the inserter and there is no need to align the device or for example to rearrange or correct the horizontal arms of a T or a 7-shaped device. The IUS is positioned at the forward end of the plunger in the expanded configuration and with the lower end of the device abutting the end of the plunger. In case of intrauterine systems having for example the shape of T or 7, the elongate member and the hormone cylinder are preferably protected by the insertion tube and the wing(s) of the transverse member remain outside the insertion tube in expanded configuration in order to prevent fatigue. The removal string(s) attached to the device, running in the groove of the plunger and ending at the end of the handle, are immobilised by the locking means to keep the IUS at a steady and correct position until it is released in the uterus.

Then, the handle is held tightly and the insertion tube is moved towards the IUS by pushing the slider forwards until the first pair of stop members gets together, thereby stopping the movement of the insertion tube. At this moment the IUS is substantially inside the insertion tube, and ready for insertion. The distance the slider can be moved forwards from the preliminary position substantially corresponds to the length of the IUS assembled for insertion. This ensures that the front edge of the insertion tube, the edge toward the uterus, is stopped in a configuration in which upper ends of the intrauterine system or the hemispherical tips of the wings remain partly uncovered by the insertion tube, but nevertheless remain pressed against each other.

The inserter is introduced into the uterus until the IUS is in the correct location, which is determined beforehand by using a probe. To release the IUS the insertion tube is drawn backwards by retracting the slider towards the handle all the way until the second pair of stop members gets together. The movement of the slider also releases the locking means thus releasing the removal string(s). The distance the slider or the insertion tube moves has been selected so that at this point the IUS has completely been released from the insertion tube.

The inserter thus allows easy and secure positioning of an IUS. The use of the slider mechanism is straightforward and the locking means to hold the string(s) and the IUS immobile long enough as well as the predetermined distance the insertion tube can be moved in each step guarantee an accurate positioning of the IUS during insertion and its accurate release. The stop members and the designed frontal end of the plunger control the correct positioning of the IUS in the insertion tube. Hence it is not necessary to provide so much clearing between the plunger and the insertion tube as in conventional inserters in which the IUS is positioned by retraction without any stop member. This results in an extremely stable construction, which involves no risk of irremediable bending of the tube.

DETAILED DESCRIPTION OF THE DRAWING

In the following description, the term slider and the corresponding reference number are used to designate both the slider itself and the means to move the slider attached to the slider. The term slider is thus used for convenience of reading.

FIG. 1 illustrates a general overview of an inserter according to the invention. The inserter comprises a handle 3, a plunger 2 attached to the handle, a slider 5, an insertion tube 6 around the plunger, the second end of the insertion tube being attached to the slider or to the means to move the slider. The inserter also comprises means for reversibly locking the string(s) (not shown) in such a way that the IUS remains immobile in relation to the plunger during the necessary steps prior to and during insertion, and again for releasing the string(s) and the IUS after it has been inserted. The inserter further comprises an opening 8 in a part of the handle, a channel 9 in which the insertion tube slides in the longitudinal direction, and a flange 4, which can be adjusted so that its distance from the first end of the insertion tube corresponds to the depth of the uterus.

The part of the handle 3 that is closer to its first end has an opening 8 having a first end 8a and a second end 8b, which opening runs in the direction of the plunger 2. The surface of the first end 5a of the slider 5 and the surface at the first end 8a of the opening 8 together form a first pair of stop members, and the surface of the second end 5b of the slider 5 and the surface at the second end 8b of the opening 8 together form a second pair of stop members. When inserting the IUS, the slider and the insertion tube can be moved forward until the surfaces 8a and 5a contact each other, and backwards until the surfaces 5b and 8b contact each other. The locking means are arranged inside the handle 3 and are thus not visible.

Figure 2A:
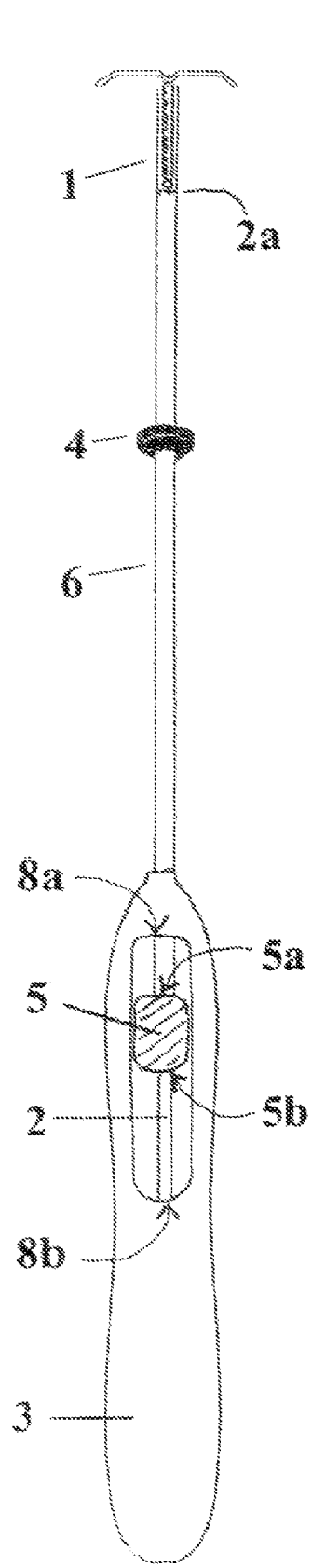
FIGS. 2A, 2B and 2C illustrate an operating principle of an inserter according to an embodiment of the invention.
Figure 2B:
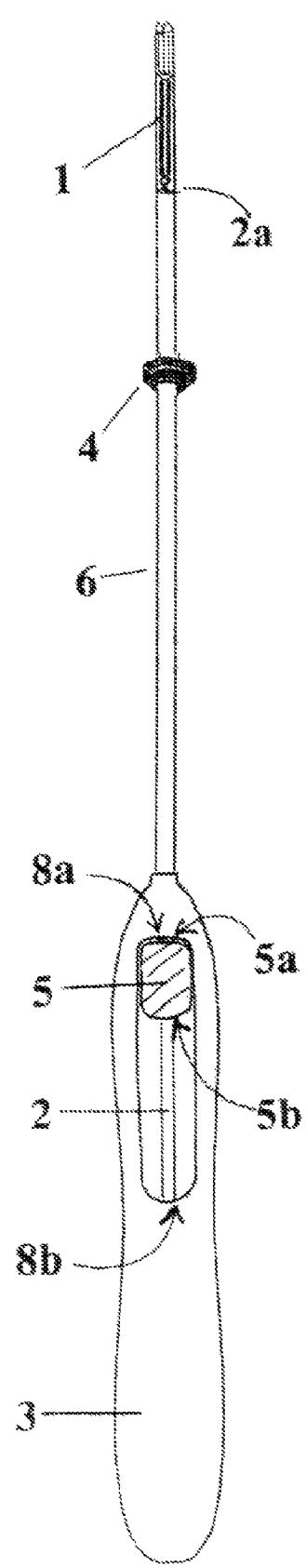
Figure 2C:
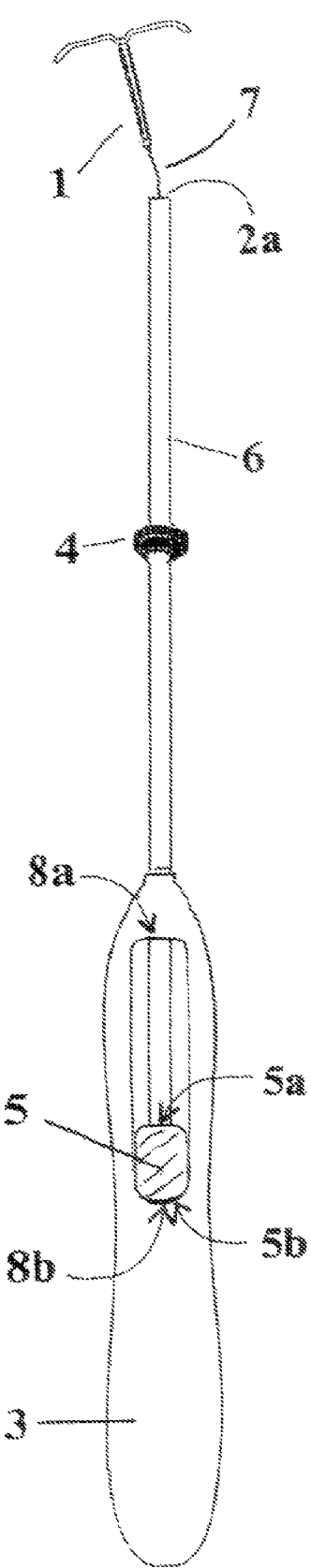

FIGS. 2A, 2B and 2C illustrate an operating principle of an inserter according to an embodiment of the invention.

FIG. 2A shows an inserter and a T-shaped IUS 1 in a configuration as they are in a sterilized package. The IUS is placed in the first end (i.e. the front end, i.e. the end of entry into the uterus) of the inserter so that the elongate member of the device with a drug containing reservoir is inside the insertion tube 6 with the tip of the elongate member abutting the end of the plunger (shown with reference number 2a). The means to move the slider 5 is on the starting or initial position, and the removal string(s) inside the inserter are tightened and locked by the locking means (not shown in the Figure).

FIG. 2B illustrates the first step of insertion procedure. While holding the handle 3, the insertion tube is moved towards the IUS by pushing the slider forward until surface 5a abuts the surface 8a of the opening 8 of the handle 3, thereby stopping the movement of the insertion tube. At this moment the IUS is substantially inside the insertion tube, and ready for insertion. The distance the slider and the insertion tube will move between the surfaces 5a and 8a has been designed substantially to correspond to the length of the IUS assembled for insertion. The first end of the insertion tube is stopped at a level at which the hemispherical tips (10a, 10b as shown in FIGS. 4A and 4B) of the wings of the IUS partly remain uncovered by the insertion tube, while the wings still remain together.

FIG. 2C illustrates the procedure to release the IUS. The device in the configuration according to FIG. 2B is introduced into the uterus until the IUS is in the correct location, where after the device is released from the insertion tube. While retaining the inserter stationary, the insertion tube is retracted towards the handle by moving the slider 5 backwards until the surface 5b of the slider abuts the surface 8b of the opening 8 of the handle 3. The distance the slider and the insertion tube can be moved has been selected to indicate clearly the moment at which the IUS has completely been released from the insertion tube moving towards the handle.

Figure 3A:
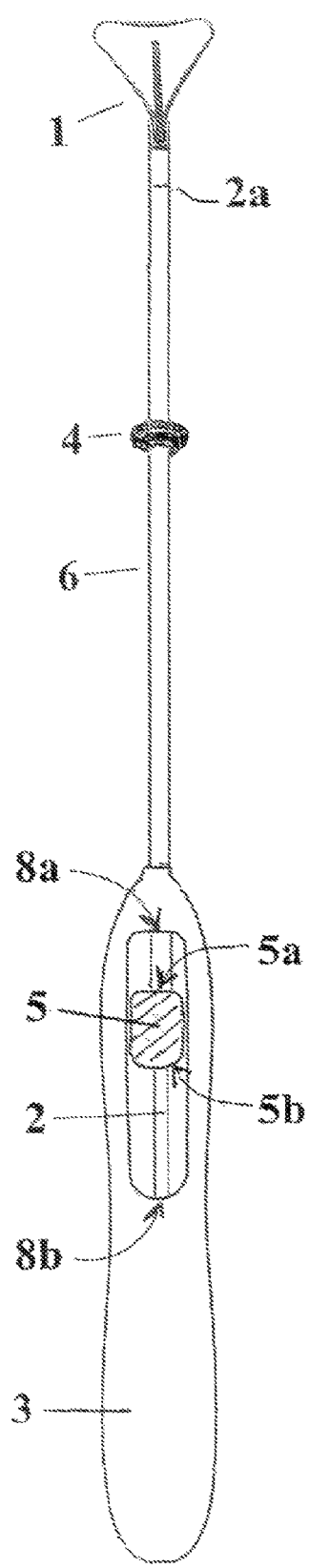
FIGS. 3A, 3B and 3C illustrate an operating principle of the inserter shown in FIGS. 2A, 2B and 2C for insertion of another type of intrauterine system.
Figure 3B:
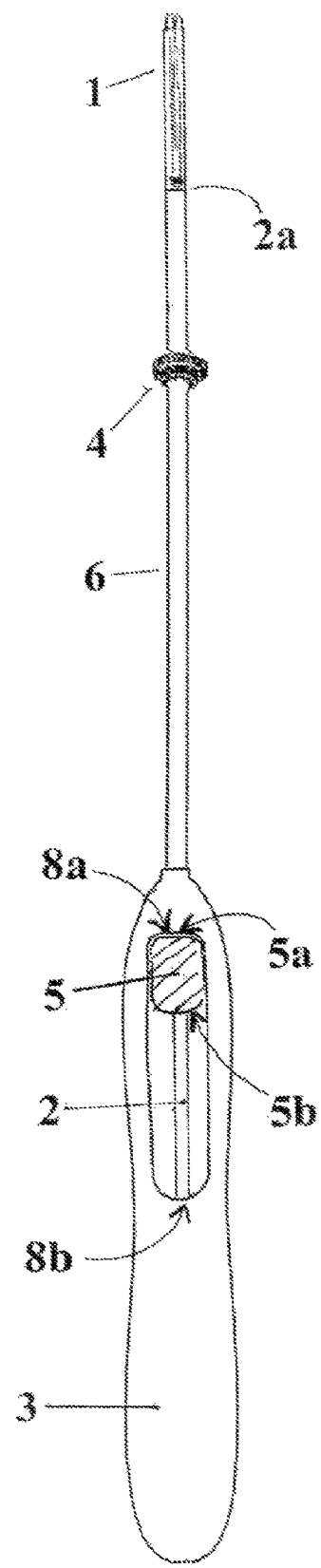
Figure 3C:
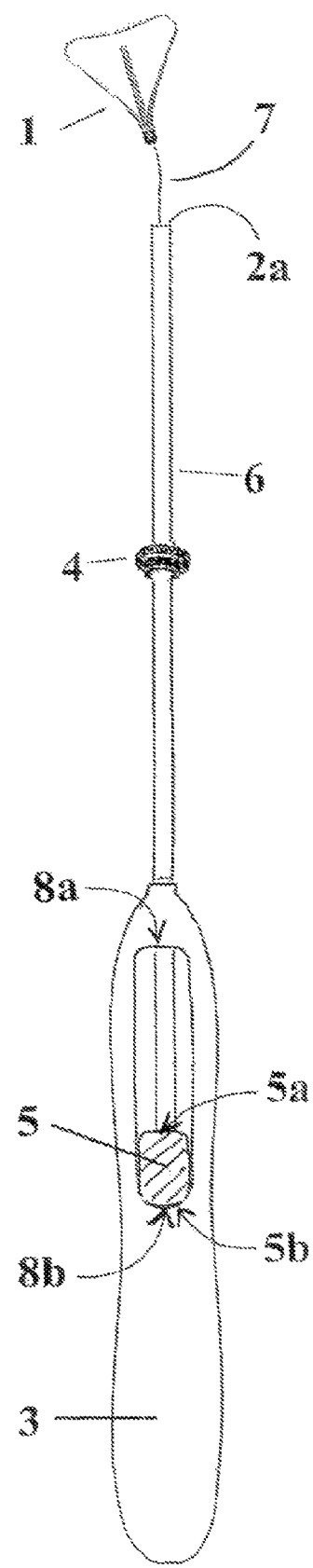

FIGS. 3A, 3B and 3C illustrate an operating principle of the inserter shown in FIGS. 2A, 2B and 2C for insertion of another type of intrauterine system. For this intrauterine system, the triangular frame of the IUS can be bent such that the frame is two-fold on its whole length when ready for insertion, or such that it is four-fold on the top half of its length.

Figure 4A:
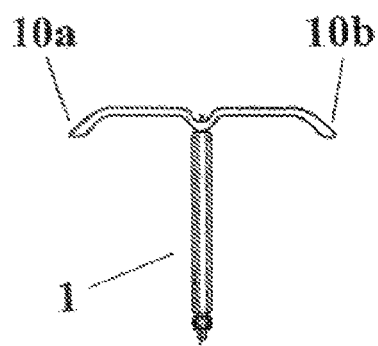
FIGS. 4A, 4B, 4C and 4D illustrate a correct positioning of an IUS in an insertion tube of an inserter according to the present invention.
Figure 4B:
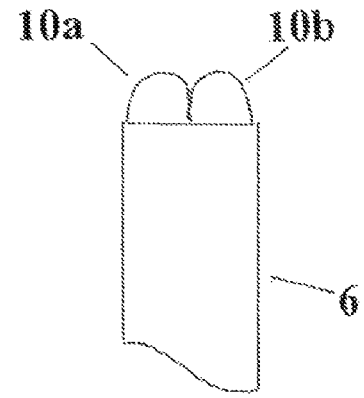
Figure 4C:
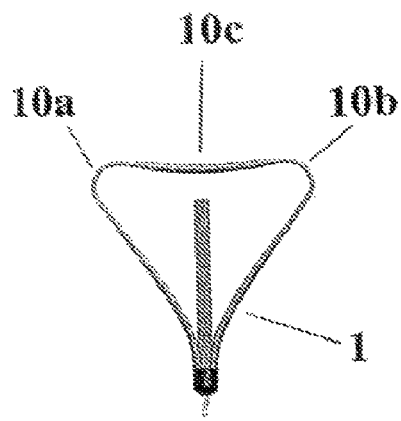
Figure 4D:
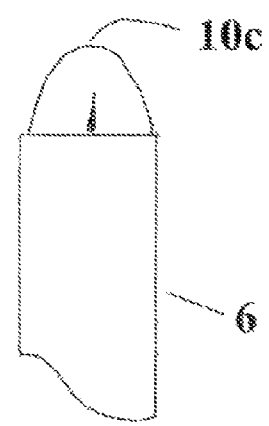

FIGS. 4A, 4B, 4C and 4D illustrate a correct positioning of an IUS in an insertion tube of an inserter according to the present invention. FIG. 4A shows one type of IUS 1 and FIG. 4B its position in an insertion tube: the first end of the insertion tube 6 is stopped at a level at which the hemispherical tips 10a, 10b of the wings of a T-shaped IUS partly remain uncovered by the protective tube 6. FIG. 4C presents another type of IUS 1, having a frame with triangular shape. In FIG. 4D is shown how the outer end 10c of the retracted and compressed closed frame partly remain uncovered by the protective tube 6.

FIGS. 5A and 5B illustrate a locking means according to an embodiment of the invention. The locking means are arranged preferably inside of the handle 3, on any of the inside surfaces of the handle. The locking means are used to immobilise and release the string(s) of the IUS.

FIG. 5A illustrates a locking means according to an embodiment of the invention comprising a main part 11 having essentially the shape of a cylinder and comprising an opening 12 there through in a diagonal direction. The string(s) 7 of the IUS pass through the opening 12. The main part 11 is rotatably mounted on the handle, on a shaft or an axle (not shown). The locking means also comprises a counterpart 13, such that in the locking position the string(s) are immobilized between the counterpart and the main part. The counterpart thus has a suitable shape adapted to fit to a part of the surface of the main part. When the slider is moving backwards, at a suitable point a part or an extension of the slider is pressed against the extension 11a of the main part 11 thus turning it enough to release the string(s), as shown in FIG. 5B.

FIGS. 6A and 6B illustrate a locking means according to another embodiment of the invention. FIG. 6A illustrates an object similar to the one presented in FIG. 5A, but having a different construction of the extension 11a.

Figure 7A:
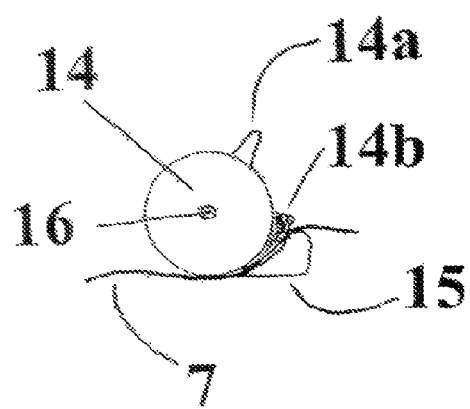
FIGS. 7A and 7B illustrate a locking means according to yet another embodiment of the invention.
Figure 7B:
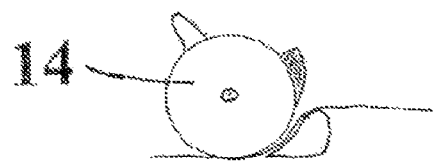

FIGS. 7A and 7B illustrate a locking means according to yet another embodiment of the invention. This is a side view of a locking means having a cylindrically shaped main part 14 which comprises two extensions 14a and 14b. The main part 14 can rotate around a shaft or an axle 16 and is preferably attached to a shorter side of the inner surface of the handle. The locking means also comprises a counterpart 15 such that the string(s) 4 are immobilised between the counterpart 15 and the extension 14b. The counterpart 15 has a suitable shape adapted to fit to a part of the surface of the extension 14b. When the slider is moving backwards, at a suitable point a part or an extension of the slider is pressed against the extension 14a thus turning it enough to release the string(s), as shown in FIG. 7B. In this case the handle can also comprise a groove in which the string(s) run (not shown).

Figure 8A:
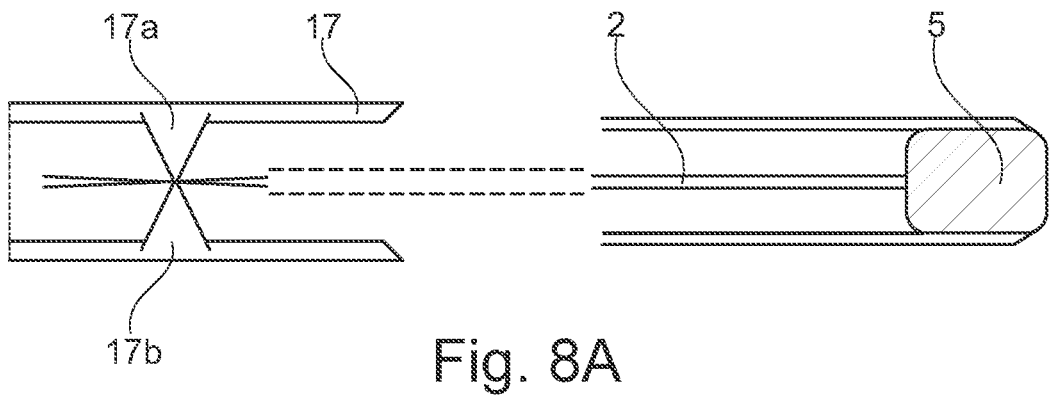
FIGS. 8A and 8B illustrate a locking means according to a further embodiment of the invention.
Figure 8B:
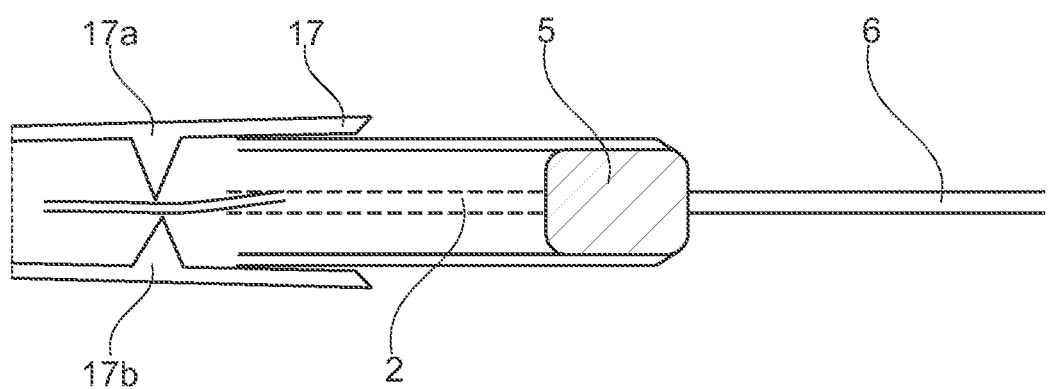

FIGS. 8A and 8B illustrate a locking means according to a further embodiment of the invention. The locking means 17 comprises two extensions 17a and 17b to immobilize the strings as shown in FIG. 8A. When the slider 5 and the insertion tube 6 move backwards the slider protrudes into the locking means at least partly to expand the means enough to separate the extensions 17a and 17b and to release the strings, as shown in FIG. 8B.

Figure 9A:
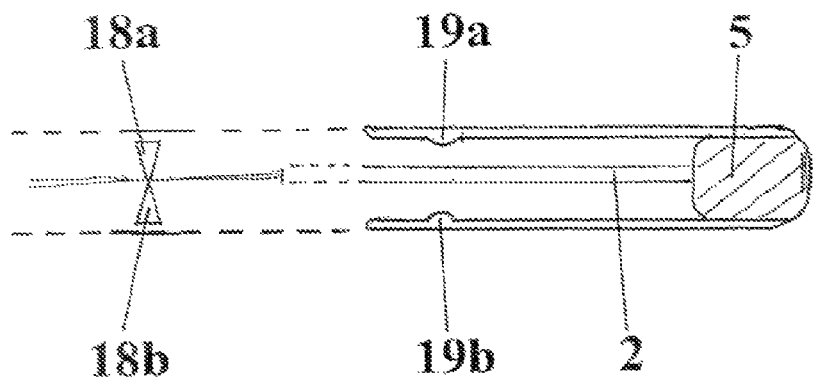
FIGS. 9A and 9B illustrate a locking means according to yet another embodiment of the invention.
Figure 9B:
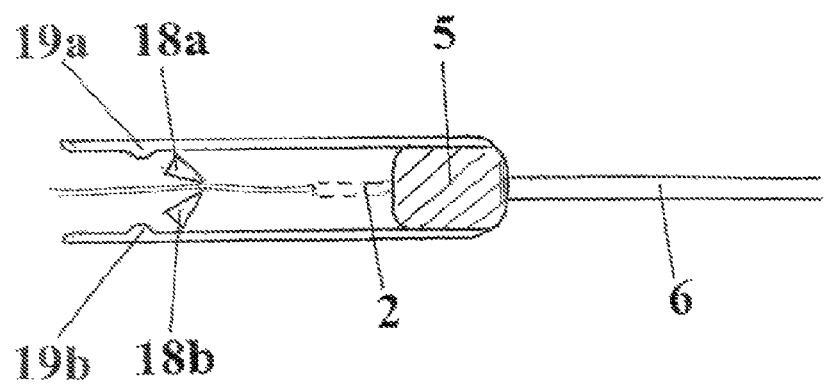

FIGS. 9A and 9B illustrate a locking means according to a yet another embodiment of the invention. The locking means comprises two parts 18a and 18b to immobilize the strings as shown in FIG. 9A, said parts being able to move or turn from their original position. The slider 5 has two extensions 19a and 19b. When the slider 5 and the insertion tube 6 move backwards the slider extensions turn the locking parts 18a and 18b apart from each other, enough to release the strings, as shown in FIG. 9B.

Figure 10:
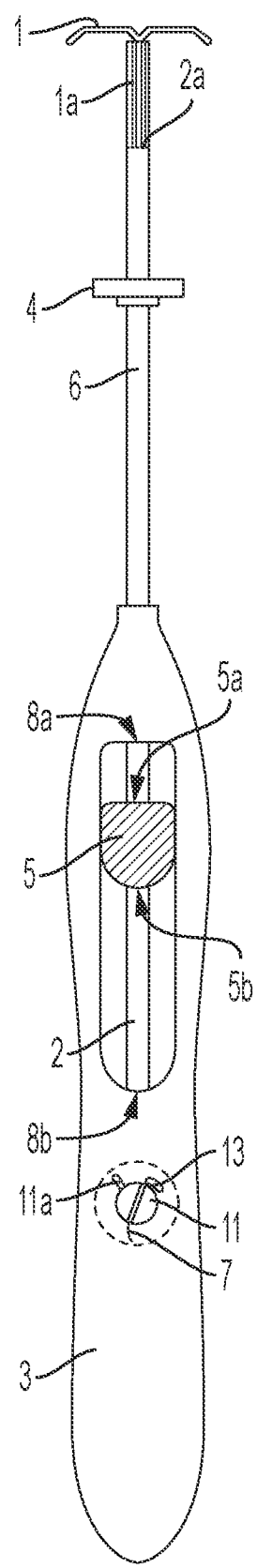
FIG. 10 illustrates a cross-section of an inserter according to an embodiment of the invention.

FIG. 10 shows a cross-section of an inserter and a T-shaped intrauterine system 1. The intrauterine system 1 includes a reservoir 1a containing a hormone. A dashed circle indicates an area inside the handle 3 where the lock is arranged. The lock is arranged inside the handle 3 and adapted to reversibly lock the intrauterine system 1 in relation to the plunger 2. The main part 11 is mounted on a shaft or axle on the handle 3.

The invention claimed is:

1. A kit comprising:
an intrauterine system comprising:
 a reservoir containing a hormone; and
 a removal string attached to the intrauterine system; and
an inserter comprising:
 a handle comprising:
  a longitudinal opening; and
  a slider arranged in the longitudinal opening;
 a plunger attached to the handle;
 an insertion tube attached to the slider; and
 a lock arranged inside the handle and adapted to reversibly lock the intrauterine system in relation to the plunger via the removal string, the lock being controllable by the slider, the lock comprising:
  a main part that is rotatably mounted on a shaft or an axle on the handle, an extension, and
  a counterpart,
  wherein the removal string is immobilized between the main part and the counterpart when the lock is in a locked position, and
  wherein the removal string is released when a part of the slider presses against the extension to turn the main part around the shaft or the axle.

2. The kit of claim 1, wherein the hormone is levonorgestrel.

3. The kit of claim 1, wherein the reservoir further comprises an elastomer.

4. The kit of claim 3, wherein the elastomer is poly(dimethylsiloxane).

5. The kit of claim 1, wherein moving the slider forward causes the lock to move into the locked position.

6. The kit of claim 1, wherein moving the slider backwards causes the lock to move into a released position.

7. The kit of claim 1, further comprising a flange arranged on the insertion tube that is adjustable such that its distance from a front end of the intrauterine system corresponds to a depth of a uterus.

8. The kit of claim 1, wherein the handle forms a channel in which the insertion tube slides in a longitudinal direction.

9. The kit of claim 1, wherein the main part comprises an opening through which the removal string passes.

10. The kit of claim 1, wherein the shaft or the axle is irregularly shaped.

11. A method for positioning an intrauterine system within a uterus, the method comprising:

(a) providing an intrauterine system having a reservoir containing a hormone and a removal string attached to the intrauterine system;
(b) sounding the uterus to determine a depth for placement of the intrauterine system;
(c) holding an inserter in one hand, the inserter comprising:
 a handle comprising:
  a longitudinal opening, the longitudinal opening having a first end and a second end; and
  a slider arranged in the longitudinal opening, the slider being movable and having a first end and a second end;
 a plunger attached to the handle;
 an insertion tube attached to the slider; and
 a lock arranged inside the handle and adapted to reversibly lock the intrauterine system in relation to the plunger via the removal string, the lock being controllable by the slider, the lock comprising:
  a main part that is rotatably mounted on a shaft or an axle on the handle,
  an extension, and
  a counterpart,
  wherein the removal string is immobilized between the main part and the counterpart when the lock is in a locked position, and
  wherein the removal string is released when a part of the slider presses against the extension to turn the main part around the shaft or the axle;
(d) introducing the inserter into the uterus with the one hand until the intrauterine system is at the depth determined in step (b); and
(e) moving the slider with one digit of the one hand, thereby releasing the removal string and intrauterine system within the uterus.

12. The method of claim 11, wherein the hormone is levonorgestrel.

13. A method of providing contraception in a patient, comprising:

(a) providing an intrauterine system having a reservoir comprising a hormone and a removal string attached to the intrauterine system;
(b) sounding a uterus to predetermine a depth for placement of the intrauterine system;
(c) holding an inserter in one hand, the inserter comprising:
 a handle comprising:
  a longitudinal opening, the longitudinal opening having a first end and a second end; and
  a slider arranged in the longitudinal opening, the slider being movable and having a first end and a second end;
 a plunger attached to the handle;
 an insertion tube attached to the slider; and
 a lock arranged inside the handle and adapted to reversibly lock the intrauterine system in relation to the plunger via the removal string, the lock being controllable by the slider, the lock comprising:
  a main part that is rotatably mounted on a shaft or an axle on the handle,
  an extension, and
  a counterpart,
  wherein the removal string is immobilized between the main part and the counterpart when the lock is in a locked position, and wherein the removal string is released when a part of the slider presses against the extension to turn the main part around the shaft or the axle;

(d) introducing the inserter into the uterus with the one hand until the intrauterine system is at the depth predetermined in step (b); and (e) moving the slider with one digit of the one hand, thereby releasing the removal string and intrauterine system within the uterus.

14. The method of claim 13, wherein the hormone is levonorgestrel.

15. A method of preventing pregnancy in a patient, comprising:

(a) providing an intrauterine system having a reservoir comprising a hormone and a removal string attached to the intrauterine system;

(b) sounding a uterus to predetermine a depth for placement of the intrauterine system;

(c) holding an inserter in one hand, the inserter comprising:
   a handle comprising:
      a longitudinal opening, the longitudinal opening having a first end and a second end; and
      a slider arranged in the longitudinal opening, the slider being movable and having a first end and a second end;
   a plunger attached to the handle;
   an insertion tube attached to the slider; and
   a lock arranged inside the handle and adapted to reversibly lock the intrauterine system in relation to the plunger via the removal string, the lock being controllable by the slider, the lock comprising:
      a main part that is rotatably mounted on a shaft or an axle on the handle,
      an extension, and
      a counterpart,
   wherein the removal string is immobilized between the main part and the counterpart when the lock is in a locked position, and
   wherein the removal string is released when a part of the slider presses against the extension to turn the main part around the shaft or the axle;

(d) introducing the inserter into the uterus with the one hand until the intrauterine system is at the depth predetermined in step (b); and (e) moving the slider with one digit of the one hand, thereby releasing the removal string and intrauterine system within the uterus.

16. The method of claim 15, wherein the hormone is levonorgestrel.

* * * * *